United States Patent [19]

Chandra et al.

[11] Patent Number: 4,593,084

[45] Date of Patent: Jun. 3, 1986

[54] PLATINUM-PHOSPHINE-VINYLSILOXANE COMPLEXES

[75] Inventors: Grish Chandra; Peter Y. K. Lo, both of Midland, Mich.

[73] Assignee: Doe Corning Corporation, Midland, Mich.

[21] Appl. No.: 672,561

[22] Filed: Nov. 19, 1984

[51] Int. Cl.$^4$ .................. C08G 77/06; C07F 15/00
[52] U.S. Cl. .................. 528/15; 556/12; 556/13; 556/14
[58] Field of Search ............... 260/429 R; 528/15, 31, 528/32; 556/136, 14, 13, 12

[56] References Cited

U.S. PATENT DOCUMENTS

| | | | |
|---|---|---|---|
| 3,159,601 | 12/1964 | Ashby | 260/429 R X |
| 3,220,972 | 11/1965 | Lamoreaux | 260/429 R X |
| 3,519,663 | 7/1970 | O'Brien et al. | 260/429 R |
| 3,522,327 | 7/1970 | Parasko | 260/429 R X |
| 3,652,615 | 3/1972 | Parasko | 260/429 R |
| 3,775,452 | 11/1973 | Karstedt | 260/429 R |
| 3,795,656 | 3/1974 | Martin | 260/429 R X |
| 3,856,837 | 12/1974 | Chandra | 260/429 R |
| 3,891,684 | 6/1975 | Jung | 260/429 R |
| 4,288,345 | 9/1981 | Ashby et al. | 260/429 R X |
| 4,394,317 | 7/1983 | McAfee et al. | 260/429 R |

OTHER PUBLICATIONS

Malatesta et al., *Journal of the Chemical Society;* 1186 (1957).

Fitch et al., *Journal of Organometallic Chemistry;* 160, 477 (1978).

*Primary Examiner*—Helen M. S. Sneed
*Attorney, Agent, or Firm*—George A. Grindahl

[57] ABSTRACT

A new method for making platinum-phosphine complexes and novel platinum-phosphine-vinylsiloxane complexes are disclosed. These complexes can be used in curable silicone compositions, thus providing curable silicone compositions of greatly enhanced stability at room temperature. The ability of the compositions to cure at elevated temperatures is not significantly compromised.

33 Claims, No Drawings

PLATINUM-PHOSPHINE-VINYLSILOXANE COMPLEXES

BACKGROUND OF THE INVENTION

The present invention relates to an improved method for making platinum-phosphine complexes and to certain platinum-phosphine-vinylsiloxane complexes.

The term platinum-phosphine complexes and platinum-phosphine-vinylsiloxane complexes, as used herein refers to complexes wherein the platinum atom in the complex has a formal oxidation state of zero.

Platinum-phosphine complexes have been known for many years. For example, Malatesta et al., Journal of the Chemical Society, 1957, 1186, disclose the synthesis of platinum-phosphine complexes.

Exemplary of known methods for making platinum-phosphine complexes is the reduction of a phosphine-complexed platinous chloride, said reduction being performed by a mixture of hydrazine, alcoholic potassium hydroxide, and an excess of non-complexed phosphine. Another known method, suitable for making trialkylphosphine complexes of platinum, is the displacement of boroallyl ligands on platinum by phosphines.

Another known method uses platinum-phosphine-olefin complexes as starting materials. An example of this method is the work of Fitch et al., as disclosed in the Journal of Organometallic Chemistry, 1978, 160, 477. Fitch et al. reacted vinylsilanes with platinum-phosphine-olefin complexes wherein the vinylsilanes have the general formula $CH_2=CHSi(CH_3)_y(OC_2H_5)_{3-y}$, y having a value of 0, 1, 2 or 3.

Each of these known methods of making platinum-phosphine complexes is fraught with difficulty: yields are low; starting materials are difficult to synthesize, difficult to handle and difficult to obtain; and the reactions are prone to side reactions in the presence of small amounts of contaminants. For example, small amounts of water can hydrolyze and cause condensation of the ethoxy-substituted vinylsilanes of Fitch et al., thus rendering Fitch et al's complexes either less useful, or totally useless.

SUMMARY OF THE INVENTION

It is an object of the present invention to provide a new and improved method for making platinum-phosphine complexes. It is a further object to provide a method for making platinum-phosphine-vinylsiloxane complexes. It is another object to provide novel platinum-phosphine-vinylsiloxane complexes. It is yet another object to provide curable silicone compositions that have enhanced stability at room temperature.

These objects and others are attained by the method and complexes of the present invention. The method of the present invention comprises contacting certain phosphines and platinum-vinylsiloxane complexes with one another in an oxygen-free environment. The complexes of the present invention are certain platinum-phosphine-vinylsiloxane complexes.

DETAILED DESCRIPTION OF THE INVENTION

The present invention relates to a method for making platinum complexes, said method comprising contacting a platinum-vinylsiloxane complex with a phosphine selected from the group consisting of $R_3P$ molecules and $R_2P(CH_2)_mPR_2$ molecules wherein each R is selected from the group consisting of monovalent hydrocarbon radicals free of aliphatic unsaturation and m has a value of 1, 2, or 3, said contacting being accomplished in a substantially oxygen-free environment.

The present invention further relates to platinum complexes having the general formula $T_aPtQ_b$, wherein in said general formula T is a phosphine selected from the group consisting of phosphines having the formula $R_3P$ and phosphines having the formula $R_2P(CH_2)_mPR_2$, each R being a monovalent hydrocarbon radical free of aliphatic unsaturation and m having a value of 1, 2, or 3;

a has a value of 1 or 2;

Q is a vinylsiloxane; and b has a value of 1 or 2.

The method of the present invention comprises contacting a platinum-vinylsiloxane complex with a phosphine.

Platinum-vinylsiloxane complexes are well known. Platinum-vinylsiloxane complexes are the result of reacting hexachloroplatinic acid with a vinylsiloxane having the general unit formula $R_n'SiO_{(4-n)/2}$, wherein each R' is a monovalent hydrocarbon radical; each n has a value of 1, 2, or 3; there is at least one R' unit in said vinylsiloxane having the formula $CH_2=CH-$, and there is at least one SiOSi linkage present in said vinylsiloxane.

Platinum-vinylsiloxane compounds have been described in U.S. Pat. No. 3,419,593, issued Dec. 31, 1968 to David N. Willing, the specification of which patent is hereby incorporated herein to further teach a method for making suitable platinum-vinylsiloxane complexes. U.S. Pat. No. 3,775,452, issued Nov. 27, 1973 to Karstedt also discloses methods for making suitable platinum-vinylsiloxane complexes.

In general, platinum-vinylsiloxane complexes are made by contacting a vinylsiloxane with a suitable platinum compound such as hexachloroplatinic acid. Hexachloroplatinic acid is well known and widely available commercially.

R' in the above general unit formula for the vinylsiloxane is a monovalent hydrocarbon radical. Thus, R' can be an alkyl radical, such as methyl, ethyl, propyl or butyl; an aryl radical such as phenyl or naphthyl; a cycloalkyl radical, such as cyclohexyl, cycloheptyl, and the like; an alkenyl radical, such as vinyl or allyl; or a cycloalkenyl radical, such as cyclohexenyl, cycloheptenyl and the like. At least one R' of each vinylsiloxane, on average, must be a vinyl radical.

The vinylsiloxane can be linear, branched or cyclic in structure. Examples of appropriate vinylsiloxanes include the following. The term Vi in the following examples of vinylsiloxanes and in this specification represents the $CH_2=CH-$ radical; the term Me represents the $CH_3-$ radical.

$ViMe_2SiOSiMe_2Vi$;

$ViMe_2SiO(SiMeViO)_7SiMe_2Vi$; $ViMe_2SiO(SiMeO)_3SiMe_3$;
$\qquad\qquad\qquad\qquad\qquad\qquad\qquad\quad |$
$\qquad\qquad\qquad\qquad\qquad\qquad\qquad\quad OSiMe_3$ $(MeViSiO)_3$; $(MeViSiO)_4$, the last two formulae representing cyclosiloxanes; and other structures.

Phosphines suitable for use in the method of the present invention are selected from those phosphines having the formula $R_3P$, and those phosphines having the formula $R_2P(CH_2)_mPR_2$, m having a value of 1, 2, or 3.

R in each of the above formulae is a monovalent hydrocarbon radical free of aliphatic unsaturation. Thus, R can be an alkyl radical, such as methyl, ethyl, propyl, isopropyl, butyl, isobutyl, tertiary butyl, hexyl, heptyl, and the like. R can also be a cycloalkyl radicals, such as cyclopentyl, cyclohexyl, cycloheptyl, and the like. R can also be an aryl radical, such as phenyl, naphthyl and the like. R can also be an alkaryl radical, such as tolyl, xylyl, or mesityl. R can also be an aralkyl radical, such as betaphenylethyl, beta-phenylpropyl and the like.

Phosphines as above described are well known and widely available. Moreover, their synthesis is well known in the organic chemistry art.

Especially preferred phosphines for the method of the present invention are those in which R is selected from the group consisting of phenyl, cyclohexyl, and tertiary butyl radicals.

The contacting referred to in performing the method of the present invention is done by simply exposing the two reactants to one another as by simply mixing. Mixing can be accomplished manually, by placing the two reactants in a single vessel and swirling or shaking. More preferably, mixing is accomplished with a mechanical stirrer or mixer.

The method of the present invention comprises contacting the phosphine, as described above, with the platinum vinylsiloxane, as described above, in a substantially oxygen-free environment.

By substantially oxygen-free environment it is meant herein no more than 20 or 30 parts per million by weight of the environment in which the method of the present invention is being performed can be $O_2$, molecular oxygen. Preferably, the $O_2$ concentration is less than 20 parts per million.

While not required, it is most convenient to perform the method of the present invention in an enclosed vessel, equipped with a stirrer, under a blanket of inert gas. Examples of commonly used inert gasses include nitrogen, helium, and argon. It is also frequently convenient to perform the method of the present invention with the two reactants dissolved in a suitable solvent.

Suitable solvents for use in the method of the present invention are those that will dissolve the two reactants, and will not appreciably react with either of the two reactants. Many common industrial solvents are suitable. For example, hexane, heptane, octane, toluene, benzene, xylene, acetone, and methyl-ethyl ketone are all suitable. Selection of the solvent, if a solvent is used, is not critical.

The method of the present invention can be performed at room temperature, or the temperature can be elevated. If the temperature is elevated, it is necessary to limit the temperature to avoid thermal decomposition of any of the reactants. If a solvent is used, it is desirable to provide a condenser for solvent vapors, and means to return the condensed solvent vapors to the enclosed vessel.

The reactants to be contacted with one another are combined in approximately, i.e. ±10%, stoichiometric amounts. Thus, if it is desired to produce the complex Pt(PPh$_3$)$_3$, wherein Ph represents the phenyl radical, approximately three moles of PPh$_3$ are added to each mole of Pt present in the platinum-vinylsiloxane complex. If it is desired to produce the complex PtP(tBu)$_3$.(Me$_2$ViSi)$_2$O, wherein tBu represents the tertiary butyl radical and Vi represents the vinyl radical, and Me represents the methyl radical, then approximately one mole of P(tBu)$_3$ are added to each mole of Pt present in a platinum-vinylsiloxane complex wherein the vinylsiloxane is (Me$_2$ViSi)$_2$O.

The reaction in the method of the present invention is fairly rapid, and is generally completed in less than an hour. Simple routine experimentation can be used to determine optimum reaction conditions or reaction times, if such are desired.

If it is desired that platinum-phosphine-vinylsiloxane complexes be produced in the method of the present invention, phosphines having relatively sterically large groups should be used, e.g. tertiary butyl or cyclohexyl groups. Conversely, if a platinum-phosphine complex is desired, phosphines substituted with relatively sterically small groups should be used, e.g. methyl or ethyl.

Compositions of the present invention have the general formula $T_aPtQ_b$, wherein T is a phosphine selected from the group consisting of phosphines having the formula $R_3P$ and phosphines having the formula $R_2P(CH_2)_mPR_2$, each R being a monovalent hydrocarbon radical free of aliphatic unsaturation and m having a value of 1, 2, or 3;

a has a value of 1 or 2;

Q is a vinylsiloxane; and b has a value of 1 or 2.

The platinum in the above general formula will have either 3 or 4 complexation sites. Since the phosphine can be a monodentate ligand of the form $R_3P$ or a bidentate ligand of the form $R_2P(CH_2)_mPR_2$, and the vinylsiloxane can also be a monodentate or a multidentate ligand, it will be noted that the sum of a plus b can have a value of 2, 3, or 4.

Particularly preferred complexes of the present invention are

Pt(P(C$_6$H$_5$)$_3$)$_3$;

Pt((C$_6$H$_5$)$_2$PCH$_2$CH$_2$P(C$_6$H$_5$)$_2$)$_2$;

Pt(C$_6$H$_{11}$)$_3$P((CH$_2$=CH)(CH$_3$)$_2$Si)$_2$O; and

PtC(CH$_3$)$_3$P((CH$_2$=CH)(CH$_3$)$_2$Si)$_2$O.

The platinum complexes of the present invention are useful as catalysts for hydrosilylation reactions; as catalysts for hydrogenation of unsaturated organic compounds or polymers; as catalysts for the isomerization of olefins; as catalysts for the oligomerization of acetylene and other alkynes; and in many other applications which require a platinum catalyst.

The platinum complexes of the present invention resulting from the method of the present invention are especially useful as curing catalysts for curable silicone compositions comprising (1) a silicone polymer having at least one unit selected from the group consisting of CH$_2$=CH—Si≡ units and ≡SiOH units;

(2) a silicone polymer having at least one ≡SiH unit; and (3) a platinum complex formed by contacting a phosphine with a platinum-vinylsiloxane complex.

A curable silicone composition as described above is made by simply mixing the appropriate polymers and platinum complex together. Simple mixing is accomplished by mixers, such as Myers ® mixers, sigmoid blade mixers, three-roll mills, two-roll mills, Baker Perkins ® type mixers, and other known mixers.

Generally from 1 to 99 parts by weight of Component (1), from 1 to 99 parts by weight of Component (2), and a catalytically effective amount of the platinum complex are used. By catalytically effective amount it is meant herein an amount sufficient to allow the curable composition to be cured in a reasonable amount of time, such as an hour or less, at a reasonable elevated temperature, such as 35° C. or higher.

Catalytically effective amounts of the platinum-complex of the present invention vary from 1 part per million by weight of platinum metal to 0.1% by weight of platinum metal.

More preferably, the amounts of Components (1) and (2) are selected so that approximately equimolar amounts of $\equiv$SiH on the one hand and $\equiv$SiCH$=$CH$_2$ or $\equiv$SiOH on the other hand are used.

A curable composition as described above is a useful coating material, such as a paper release coating. If a reinforcing filler, such as amorphous silica, is added to the curable composition, a useful elastomer will result upon cure.

The platinum complexes produced by the method are useful catalysts for both filled an unfilled curable silicone compositions.

The following Examples are here presented to further teach the method of the present invention and the use of the products of the present invention. All parts and percentages in the Examples are by weight unless otherwise specified.

CHARACTERIZATION METHODS

The products of the method of the present invention were characterized by the following methods:

Yield: Yields were determined by dividing the weight of the product actually obtained by the weight of product which would result from complete reaction and recovery of product, and multiplying the result of this division by 100%.

Elemental Analysis: Carbon and hyrogen percentages were determined by the combustion method. The complexes being analyzed were quantitatively burned in oxygen, and the resulting weights of CO$_2$ and H$_2$O were determined. These weights were used to calculate the percentages of carbon and hydrogen originally present in the complex.

Phosphorous, platinum and silicon analyses reported herein were done by atomic absorption spectroscopy, which is a well known method for determining these elements quantitatively.

Yields reported herein were calculated on the basis of the amounts of phosphine in the reaction mixture.

The following test procedures were used to evaluate cured films in the following examples.

Smear—Smear of a coating was evaluated by lightly rubbing the cured coating with a finger. A wholly cured coating will not change in appearance upon rubbing. No change in the appearance in the smear test is recorded in the following examples as "no smear."

Rub-off—Rub-off of a coating was evaluated by vigorously rubbing the cured coating with a finger. The result "no ruboff" indicates that the coating could not be removed in this manner. The result "ruboff" indicates that the coating was easily removed.

Migration—Migration was evaluated herein by: first, adhering a strip of standard adhesive-coated tape to the cured coating by firmly pressing the side coated with adhesive to the cured coating; second, removing the tape from the cured coating by peeling the tape up; third, doubling the removed tape back upon itself with the adhesive coated side adhering to itself; and fourth, comparing the force required to peel the doubled tape to the force required to peel a freshly prepared, similarly doubled tape which had never been adhered to the coating. If the force required is substantially the same, no migration of the coating or components thereof has occurred. This result is recorded as "no migration." Total loss of adherence indicates that migration of coating components has taken place. This result is recorded as "migration."

The following terms are assigned the following meanings in the Examples for the sake of brevity:

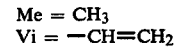

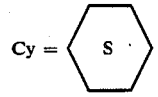

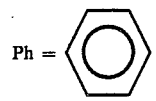

EXAMPLE 1

1.35 g of platinum -(Me$_2$ViSi)$_2$O complex mixture consisting of the complex dissolved in (Me$_2$ViSi)$_2$O and higher oligomers consisting of (Me$_2$SiO) units and Me$_2$ViSiO$_{3/2}$ units, containing 4.02% platinum, were added to a solution consisting of 0.3 g of PPh$_3$ dissolved in 10 ml of pentane, all of the above ingredients being confined to a closed vessel under a nitrogen blanket. Yellow crystals rapidly precipitated. These yellow crystals were filtered, and washed with pentane. Residual pentane was removed by exposing the yellow crystals to reduce pressure for several minutes. The calculated yield was 84.7%.

Elemental analysis for carbon and hydrogen was consistent with the structure

|  | Pt(PPh$_3$)$_3$ | |
|---|---|---|
|  | theory | found |
| % carbon | 66.06 | 66.34 |
| % hydrogen | 4.59 | 5.03 |

EXAMPLE 2

1.35 g of the platinum-vinylsiloxane complex mixture used in Example 1 were added to a solution consisting of 0.24 g of Ph$_2$PCH$_2$CH$_2$PPh$_2$ dissolved in 10 ml of toluene. Said addition was accomplished in an enclosed vessel under a nitrogen blanket. The above reactants were mechanically mixed for 30 minutes, after which time the toluene was removed under reduced pressure. The residue was a yellow solid. This yellow solid was dissolved in pentane, then isolated by the procedure of Example 1. Yield was 72.4%. Elemental analysis was consistent with the structure

|  | Pt(Ph$_2$PCH$_2$CH$_2$PPh$_2$)$_2$ | |
|---|---|---|
|  | theory | found |
| % carbon | 62.90 | 61.29 |

-continued

| Pt(Ph₂PCH₂CH₂PPh₂)₂ | | |
|---|---|---|
| | theory | found |
| % hydrogen | 4.80 | 5.40 |

COMPARISON TO EXAMPLE 2

The same reactants used in Example 2 were reacted together, in acetone, with no steps being taken to exclude oxygen from the reaction environment.

The resulting product had a melting point of 269° C.-270° C., as compared to a published value of 273° C.-274° C. for the compound Ph₂P(O)CH₂CH₂P(O)Ph₂

Elemental analysis was consistent with this structure:

| | theory | found |
|---|---|---|
| % carbon | 72.50 | 71.40 |
| % hydrogen | 5.60 | 5.76 |
| % phosphorous | 14.40 | 14.40 |

Thus it is seen that failure to perform the method of the present invention in a substantially oxygen-free environment results in an oxidized phosphine rather than a platinum complex.

EXAMPLE 3

40 g of the platinum-vinylsiloxane complex mixture used in Example 1 and 1.80 g of P(tBu)₃ were heated together, with mixing, in an enclosed vessel, under a nitrogen blanket, to a temperature of 65° C. This temperature was maintained for 5 minutes, after which time the mixture was allowed to cool to room temperature.

A white solid separated, which solid was filtered, washed with (Me₂ViSi)₂O, and the residue was exposed to reduced pressure to remove volatile substances. The product was obtained in a yield of 79.4%, and had a melting point of 145° C.-147° C.

The product was subjected to X-ray structural analysis, which analysis proved the structure to be PttBu₃P(Me₂ViSi)₂O Elemental analysis was consistent with the above structure:

| | theory | found |
|---|---|---|
| % carbon | 41.16 | 41.23 |
| % hydrogen | 7.72 | 7.57 |
| % phosphorous | 5.32 | 5.49 |
| % silicon | 9.61 | 9.50 |
| % platinum | 33.45 | 33.22 |

EXAMPLE 4

80 g of the platinum-vinylsiloxane complex used in Example 1 were heated with 5.0 g of PCy₃ under a nitrogen blanket, with mixing. After a temperature of 85° C. had been attained and held for 5 minutes, the mixture was allowed to cool. A white solid separated, which solid was treated by the procedure of Example 3.

The product was obtained at a yield of 63.2%, and had a melting point of 188° C.-189° C.

Elemental Analysis was consistent with the structure

| Pt(PCy₃(Me₂ViSi)₂O) | | |
|---|---|---|
| | theory | found |
| % carbon | 47.20 | 48.20 |
| % hydrogen | 7.72 | 7.95 |
| % phosphorous | 4.60 | 4.50 |
| % silicon | 8.47 | 8.75 |

EXAMPLE 5

0.25 g of the complex produced in Example 4 were dissolved in sufficient toluene to produce a 0.71% platinum solution.

The following components were mixed together to form a curable silicone composition:
(1) 67.9 g of a polymer having the average formula ViMe₂SiO(Me₂SiO)₁₃₅SiMe₂Vi; and 0.63 g of methylvinylcyclosiloxanes;
(2) 3.22 g of a mixture consisting of
  (a) 41.67 parts of a polymer having the average formula Me₃SiO(MeHSiO)₃₅SiMe₃; and (b) 58.33 parts of a (Me₂SiO)/(MeHSiO) copolymer having a viscosity of 5 centistokes at 25° C.
(3) 1.29 g of the 0.71% platinum solution.

The viscosity of this mixture was monitored as a function of time. Additionally, the time required to cure a thin film at 130° C. was determined periodically. The criteria for cure were no smear, no ruboff, and no migration. See Table 1.

TABLE 1

| | Cure Stability | |
|---|---|---|
| Time at 25° C. (hours) | Viscosity (Centistokes at 25° C.) | Minimum Cure Time at 130° C. |
| 0 | 304 | 70 seconds |
| 5 | 308 | — |
| 7.5 | 308 | — |
| 24 | 344 | 75 seconds |
| 32 | 308 | — |
| 64 | 420 | — |
| 82 | 580 | — |
| 154 | gelled | — |

COMPARISON TO EXAMPLE 5

The procedure of Example 5 was repeated with a platinum-vinylsiloxane complex instead of a complex of the present invention. This mixture gelled in 30 minutes.

The procedure of Example 5 was then repeated with a platinum-vinylsiloxane complex instead of a complex of the present invention. This time 2.44 parts of the inhibitor 3,5-dimethyl-1-hexyne-3-ol were included. The results of evaluation of this comparison are found in Table II.

TABLE 2

| | Cure Stability | |
|---|---|---|
| Time at 25° C. (hours) | Viscosity (centistokes at 25° C.) | Minimum Cure Time at 82° C. |
| 0 | 368 | 60 seconds |
| 5 | 476 | — |
| 7 | 516 | — |

TABLE 2-continued

| Time at 25° C. (hours) | Cure Stability Viscosity (centistokes at 25° C.) | Minimum Cure Time at 82° C. |
|---|---|---|
| 12 | gelled | — |

Thus it is seen that the complexes of the present invention greatly enhance effective life of a curable silicone composition at room temperature without seriously compromising the ability to cure at elevated temperatures.

That which is claimed is:

1. A method for making platinum-phosphine complexes, said method comprising contacting approximately stoichiometric amounts of a platinum-vinylsiloxane complex and a phosphine selected from the group consisting of $R_3P$ molecules and $R_2P(CH_2)_mPR_2$ molecules wherein each R is selected from the group consisting of monovalent hydrocarbon radicals free of aliphatic unsaturation and m has a value of 1, 2, or 3, said contacting being accomplished at room temperature or above in a substantially oxygen-free environment.

2. A method as claimed in claim 1 wherein the platinum vinylsiloxane complex is a platinum $((CH_3)_2CH_2\!=\!CHSi)_2O$ complex.

3. A method as claimed in claim 2 wherein each R is a phenyl radical.

4. A method as claimed in claim 3 wherein the phosphine is $P(C_6H_5)_3$.

5. A method as claimed in claim 2 wherein each R is a cyclohexyl radical.

6. A method as claimed in claim 5 wherein the phosphine is $P(C_6H_{11})_3$.

7. A method as claimed in claim 2 wherein each R is a tertiary butyl radical.

8. A method as claimed in claim 7 wherein the phosphine is $P\{C(CH_3)_3\}_3$.

9. Platinum complexes having the general formula $T_aPtQ_b$, wherein, in said general formula
T is a phosphine selected from the group consisting of phosphines having the formula $R_3P$ and phosphines having the formula $R_2P(CH_2)_mPR_2$, each R being a monovalent hydrocarbon radical free of aliphatic unsaturation and m having a value of 1, 2, or 3;
a has a value of 1 or 2;
Q is a vinylsiloxane; and
b has a value of 1 or 2.

10. Platinum complexes as claimed in claim 9 wherein Q is $((CH_3)_2CH_2\!=\!CHSi)_2O$, a has a value of 1, and b has a value of 1.

11. Platinum complexes as claimed in claim 10 wherein each R is a phenyl radical.

12. Platinum complexes as claimed in claim 10 wherein each R is a cyclohexyl radical.

13. A platinum complex as claimed in claim 12 having the formula $PtP(C_6H_{11})_3\{(CH_3)_2CH_2\!=\!CHSi\}_2O$.

14. Platinum complexes as claimed in claim 10 wherein each R is a tertiary butyl radical.

15. A platinum complex as claimed in claim 14 having the formula $PtP\{C(CH_3)_3\}_3\{(CH_3)_2CH_2\!=\!CHSi\}_2O$.

16. A curable silicone composition comprising
(1) from 1 to 99 parts of a silicone polymer having at least one unit selected from the group consisting of $CH_2\!=\!CHSi\!\equiv\!$ units and $HOSi\!\equiv\!$ units;
(2) from 1 to 99 parts of a silicone polymer having at least on $HSi\!\equiv\!$ unit; and
(3) a catalytically effective amount of a platinum complex having the general formula
$T_aPtQ_b$, wherein, in said general formula
T is a phosphine selected from the group consisting of phosphines having the formula $R_3P$ and phosphines having the formula $R_2P(CH_2)_mPR_2$, each R being a monovalent hydrocarbon radical free of aliphatic unsaturation and m having a value of 1, 2, or 3;
a has a value of 1 or 2;
Q is a vinylsiloxane; and
b has a value of 1 or 2.
the above parts being parts by weight.

17. A curable silicone composition as claimed in claim 16 wherein Q represents $((CH_3)_2CH_2\!=\!CHSi)_2O$, a has a value of 1 and b has a value of 1.

18. A curable silicone composition as claimed in claim 17 wherein R is a phenyl radical.

19. A curable silicone composition as claimed in claim 18 wherein the phosphine is $P(C_6H_5)_3$.

20. A curable silicone composition as claimed in claim 17 wherein R is a cyclohexyl radical.

21. A curable silicone composition as claimed in claim 20 wherein the phosphine is $P(C_6H_{11})_3$.

22. A curable silicone composition as claimed in claim 17 wherein R is a tertiary butyl radical.

23. A curable silicone composition as claimed in claim 22 wherein the phosphine is $P\{C(CH_3)_3\}_3$.

24. A curable silicone composition as claimed in claim 17 further comprising from 1 to 99 parts of a filler.

25. A curable silicone composition as claimed in claim 24 wherein the filler is amorphous silica.

26. A curable silicone composition as claimed in claim 25 wherein R is a phenyl radical.

27. A curable silicone composition as claimed in claim 27 wherein the phosphine is $P(C_6H_5)_3$.

28. A curable silicone composition as claimed in claim 25 wherein R is a cyclohexyl radical.

29. A curable silicone composition as claimed in claim 28 wherein the phosphine is $P(C_6H_{11})_3$.

30. A curable silicone composition as claimed in claim 29 wherein the platinum complex has the formula $PtP(C_6H_{11})_3\{(CH_3)_2CH_2\!=\!CHSi\}_2O$.

31. A curable silicone composition as claimed in claim 25 wherein R is a tertiary butyl radical.

32. A curable silicone composition as claimed in claim 31 wherein the phosphine is $P\{C(CH_3)_3\}_3$.

33. A curable silicone composition as claimed in claim 32 wherein the platinum complex has the formula $PtP\{C(CH_3)_3\}_3\{(CH_3)_2CH_2\!=\!CHSi\}_2O$.

* * * * *

UNITED STATES PATENT AND TRADEMARK OFFICE
CERTIFICATE OF CORRECTION

PATENT NO. : 4,593,084

DATED : June 3, 1986

INVENTOR(S) : Grish Chandra and Peter Y. K. Lo

It is certified that error appears in the above-identified patent and that said Letters Patent is hereby corrected as shown below:

On the Title Page, on the "Assignee" line, "Doe" should read --Dow--.

Signed and Sealed this

Ninth Day of September 1986

[SEAL]

Attest:

DONALD J. QUIGG

Attesting Officer

Commissioner of Patents and Trademarks